(12) United States Patent
Krasberg

(10) Patent No.: US 7,100,603 B1
(45) Date of Patent: Sep. 5, 2006

(54) SYSTEM FOR PROVIDING PROTECTION FROM REACTIVE OXYGEN SPECIES

(76) Inventor: Alan Krasberg, 100 Clement Dr., Wirtz, VA (US) 24184

( * ) Notice: Subject to any disclaimer, the term of this patent is extended or adjusted under 35 U.S.C. 154(b) by 846 days.

(21) Appl. No.: 09/652,001

(22) Filed: Aug. 31, 2000

(51) Int. Cl.
*A61M 15/00* (2006.01)

(52) U.S. Cl. ............................... 128/200.24; 128/203.12
(58) Field of Classification Search ............ 128/200.24, 128/201.27, 202.12, 262.24, 203.12; 524/959; 454/157, 337; 422/124
See application file for complete search history.

(56) References Cited

U.S. PATENT DOCUMENTS

| | | | |
|---|---|---|---|
| 1,224,180 A * | 5/1917 | Lake | 128/205.24 |
| 3,252,458 A | 5/1966 | Krasberg | |
| 4,049,402 A * | 9/1977 | Fortson | 96/156 |
| 4,206,753 A | 6/1980 | Fife | 128/201.21 |
| 4,215,409 A * | 7/1980 | Strowe | 700/285 |
| 4,269,791 A * | 5/1981 | Hills | 261/36.1 |
| 4,284,075 A | 8/1981 | Krasberg | |
| 4,345,612 A * | 8/1982 | Koni et al. | 137/101.19 |
| 4,442,856 A * | 4/1984 | Betz | 137/98 |
| 4,549,563 A * | 10/1985 | Monnier | 137/100 |
| 5,411,059 A | 5/1995 | Sever et al. | 137/599 |
| 5,503,145 A * | 4/1996 | Clough | 128/204.22 |
| 5,664,563 A | 9/1997 | Schroeder et al. | 128/204.25 |
| 5,964,222 A * | 10/1999 | Kotliar | 128/205.26 |
| 5,971,934 A | 10/1999 | Scherer et al. | 600/526 |
| 5,996,586 A * | 12/1999 | Phillips | 128/898 |
| 6,123,074 A | 9/2000 | Hete et al. | 128/205.11 |
| 6,131,571 A | 10/2000 | Lampotang et al. | 128/204.21 |
| 6,138,670 A | 10/2000 | Delauze et al. | 128/201.27 |
| 6,158,430 A | 12/2000 | Pfeiffer et al. | 128/202.27 |
| 6,221,026 B1 * | 4/2001 | Phillips | 600/532 |
| 6,254,547 B1 * | 7/2001 | Phillips | 600/532 |
| 6,283,123 B1 | 9/2001 | Van Meter et al. | 128/205.26 |
| 6,312,390 B1 * | 11/2001 | Phillips | 600/532 |
| 6,314,956 B1 | 11/2001 | Stamler et al. | 128/200.24 |

FOREIGN PATENT DOCUMENTS

| | | | |
|---|---|---|---|
| GB | 2331707 | * 6/1999 | |
| WO | WO96/06771 | 3/1996 | 128/201.27 |

OTHER PUBLICATIONS

Gardener et al, Spacecraft maximum Allowable Concentrations for Selected Airborne Contaminants, vol. 1., pp. 139–148. 1994.
US Naval Flights Surgeon Handbook: Toxicology: 2nd Edition 1998.
The Hindenberg Disaster 1937, see e.g. http://www-.clean.air.org/hindenberg.htm.
Simes et al, Elimination of Pulmonary Oxygen Toxicity, Australasian Anaesthesia, 1998.

* cited by examiner

*Primary Examiner*—Aaron J. Lewis
(74) *Attorney, Agent, or Firm*—Robert E. Bushnell, Esq.

(57) ABSTRACT

Method, apparatus and breathable compositions for protecting a person from reactive oxygen species in the body are described. The invention involves providing a person with a breathing gas composition comprising at least one fuel gas compound. Apparatus and methods for providing such breathing gas compositions are described.

43 Claims, 4 Drawing Sheets

SYSTEM FOR PROVIDING PROTECTION FROM REACTIVE OXYGEN SPECIES

CROSS-REFERENCE TO RELATED APPLICATIONS

This application refers to and relates to Disclosure Document No. 475763 filed in the U.S. Patent & Trademark Office on 19 Jun. 2000, and the Commissioner is requested to place a true copy of that Disclosure Document in this file.

BACKGROUND OF THE INVENTION

1. Field of the Invention

The present invention relates to compositions, methods and apparatus for reducing levels of reactive oxygen species in the body.

2. Description of the Related Art

It has been shown that animals on long-term well nourished, low calorie diets tend to live longer than those on other diets. They have a lower metabolism rate than control animals on normal diets, and with fewer chemical combinations taking place at the sites of energy production in the cells (the mitochondria), their blood sugar levels are lower and there are fewer combinations with proteins to produce plaque. Also, there are fewer byproducts of incomplete oxidation, including reactive oxygen species such as singlet oxygen atoms and hydroxyl radicals.

These reactive oxygen species, including free radicals, can combine chemically with organic molecules they contact (in some cases setting off deleterious chains of free radicals), thereby reducing cell functionality throughout the body and brain, and mutating nuclear and mitochondrial DNA. For the animals on such low calorie diets, it is surmised that energy production efficiency and brain function decline more slowly with age, less cell damage occurs, fewer mutations accumulate in the cells, and less plaque is formed in the arteries and throughout the body. This may be attributable to the lower levels of reactive oxygen species yielding slower formation of plaque.

One possible approach to lowering the levels of reactive oxygen species is to provide levels in the body of compounds which scavenge the reactive oxygen species, that is, which react with and neutralize the reactive species before the reactive species undergo reactions with compounds in the body. However, this approach generally requires the ingestion of scavenging compounds. It may be difficult to achieve and maintain adequate levels of compounds by ingestion. Moreover, some compounds useful as scavengers may not be suitable for ingestion.

Based on my reading of the art, what is needed is an improved method of delivering compounds to the body to lower the concentration of reactive oxygen species.

SUMMARY OF THE INVENTION

It is therefore an object of the present invention to provide an improved method of, and apparatus for, reducing levels of reactive oxygen species in an anatomical body, such as a human body.

A further object of the invention is to provide a method of and apparatus for preventing the cellular damage caused by reactive oxygen species within an anatomical body.

These objects may be achieved in the practice of present invention, with a composition, method of delivery and apparatus for delivery of the composition to the human body, while providing protection from reactive oxygen species by intentionally artificially raising the concentration of a first fuel gas compound in the tissue of an animal to a level which is above the background level of the first fuel gas compound in the tissue.

The practice of this invention contemplates providing a person with a breathing gas composition including a fuel gas which may be hydrogen, or any gas that combines with oxygen, such as methane, ethane, propane or acetylene, or a combination of these. The composition may be provided at levels of fuel gas which are not explosive, to avoid explosion risk. Alternatively, compositions which are explosive may be provided with precautions taken to explosion-proof the environment around the person.

In one embodiment of the principles of the present invention, an apparatus is provided with a source of fuel gas is provided, along with a flow restrictor and valve, and a nasal cannula or mask for providing the gas to a person. The flow rate is set by the flow restrictor based on the minimum respiration minute volume of the person to provide an exhaled breathing gas composition in which the fuel gas is below the explosive limit.

In another embodiment, the invention provides an apparatus for providing a level of fuel gas to an entire building. Here, the apparatus includes an explosion-proof blower for circulating air in the building, ducting, a return inlet to the blower, and outlets in the rooms of the building. A constant pressure source of a fuel gas is provided with a connection line to a flow-diffuser in the ducting. A flow restrictor limits the flow rate of the fuel gas to a value which does not allow the buildup of an explosive concentration of gas. A valve in the connection line is connected to the blower and remains closed when the blower is off. A valve in the connection line is connected to a flow sensor in the duct, and remains closed when there is no flow in the duct. Another valve is connected to a fuel sensors inside the building. A vent is also provided in the attic of the building to allow for escape of gases.

In another embodiment, a composition including one or more fuel gases with a density less than that of air is provided as a breathing gas. An apparatus for providing this composition includes a transparent container which is large enough for a person to be in, and which is open at the bottom to retain the breathing gas composition by buoyancy and to permit entry and egress. The apparatus also includes a flexible skirt around the lower portion, and in the container is an overflow pipe and non-return flap valve. Additionally, an explosion-proof blower recirculates the gas inside the container from an inlet muffler through a life-support system and returns the gas through a muffler/diffuser pipe. The life-support system scrubs carbon dioxide, controls temperature and humidity, adds oxygen, and may also scrub nitrogen, argon, oils and other contaminants. Alarms and readouts for the status of the gas in the container may also be provided.

BRIEF DESCRIPTION OF THE DRAWINGS

A more complete appreciation of the invention, and many of the attendant advantages, thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
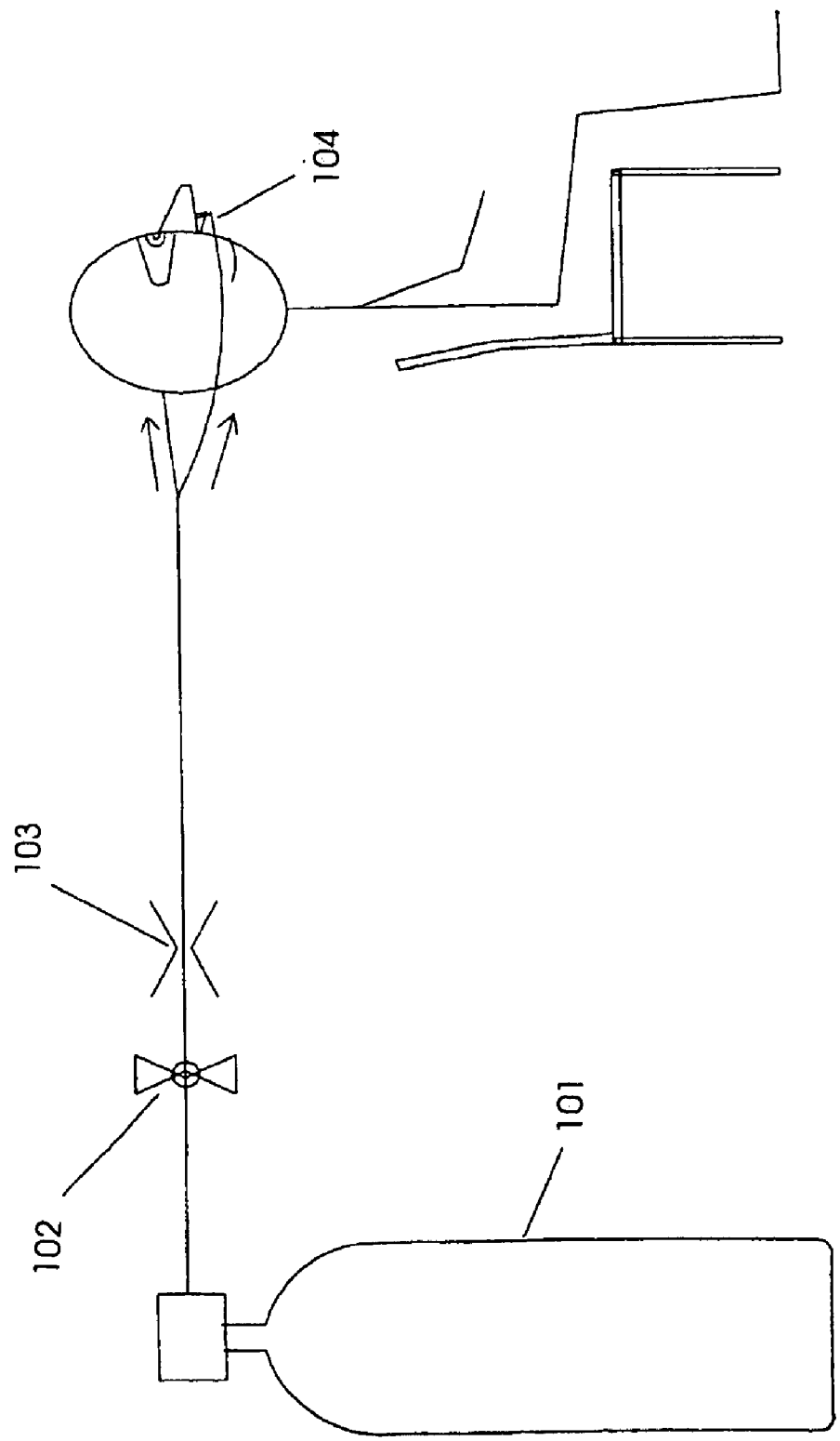
FIG. 1 is a schematic illustration of embodiments of the present invention which are an apparatus and method for delivering a breathing gas composition to an individual.

The present invention is a method to produce a beneficial effect such as that seen with low-calorie diets in animals, by neutralizing reactive oxygen species to reduce harm to the body. The present method, as will be described in detail below, involves the maintenance of concentrations in the body of one or more compounds whose purpose is to combine with and overwhelm the reactive oxygen species, and to remove them as they are produced to greatly lower the levels of these reactive oxygen species.

These compounds are fuel gas compounds, to be detailed below. Fuel gases are commonly burned with oxygen to produce heat. These are used as industrial gases, and general health and safety guidelines for these gases have been established. These gases are all classified as simple asphyxiants. [United States OSHA Regulations (Standards—29 CFR, Gases, vapors, fumes, dusts, and mists—1926.55 App A), wherein is stated, "The limiting factor is the available oxygen which shall be at least 19.5 percent and be within the requirements addressing explosion in part 1926."]. That is, the gases are not inherently toxic as long as adequate oxygen is supplied to the body, but asphyxiation will result if the gas displaces oxygen. Since these are fuel gases and burn readily, certain mixtures of the gases with oxygen will be explosive ifignited. This property of the gases will be discussed further below.

The most studied of these gases for its effects on respiration is hydrogen. Deep-sea diving trials have been conducted in which the participants were exposed to 20–40 atmospheres of hydrogen gas for weeks at a time. This illustrates that substantial concentrations of hydrogen do not appear to show any particular toxicity.

Methane and hydrogen are constituents of the atmosphere, and are also produced in the gut during digestion of certain foods, so small quantities of these two gases exist naturally in the blood stream. The wall thickness and low surface area of the gut compared to that of the lungs means that, in the balance between the methods of supply and removal, only extremely low levels of these gases can build up from digestive sources. Also, the low diffusivity of methane results in most of it leaving the body as flatus. Hydrogen can better penetrate the gut, but again, blood levels are low as the hydrogen is expelled almost immediately via the lungs. Only in completely closed environments such as diving chambers or space vehicles or where there is some other method of continuous replenishment to the lungs, can these gases achieve any substantial concentration in the body.

As a general rule, gas mixtures containing a fuel gas and oxygen are potentially explosive at adequate levels of fuel and oxygen. For example, hydrogen in air is explosive at levels of about 4 to 75% by volume, methane at 5 to 15%, ethane at 3 to 12.5%, and acetylene at 2.5 to 80%. The hydrogen deep diving trials mentioned above were performed below the explosive limit for oxygen, and thus were performed in a non flammable atmosphere. To have a life-sustaining mixture and avoid explosions at normal pressure, the breathing gas mixture must either be under the flammability limit for the fuel gas, or else one must rigidly prohibit ignition sources.

The present invention provides methods and apparatus to achieve a certain level of a fuel gas compound in solution in the body to destroy most of the reactive oxygen species while still in aqueous solution, protecting the cells from the bulk of the damage they would otherwise do. In some embodiments to be detailed below, the present invention achieves these levels at ambient pressure, unlike the conditions found, for example, in the hydrogen deep-sea trials discussed above. Even low levels of fuel gas compound in breathable gas, below the explosion limits, may raise the internal concentration of the compound well above background levels and offer useful protection.

For example, a level of hydrogen of about 1–2% in a breathing gas should yield an internal concentration that is several orders of magnitude higher than the background level occurring from natural diffusion from the gut. Higher percentages should provide higher protection, but may require using a breathing gas in the flammable range.

To achieve the desired levels of fuel gas compound in the body, one can supply the gas to the lungs for inspiration, either in an open circuit manner (for example, by a nose cannula), or in a controlled environment in homes, vehicles, places of work, public buildings, pressure vessels, space ships, full-body suits, self-contained breathing apparatus, tents (like oxygen tents), etc. Over time, the entire body equilibrates with the level of fuel gas being supplied.

Acetylene has a property which may make it particularly useful in this application. The solubility in water of acetylene at STP (standard temperature and pressure) is close to one liter/liter, a value which is 50 times higher than that of hydrogen and far higher than that of any of the other fuel gases. Water exposed to 80% acetylene at room temperature and sea level would absorb about 1 gram/liter into solution. As acetylene is several times more soluble in fat than in water, a 100 kg man in these conditions would absorb perhaps 200 grams of acetylene.

Cellular energy production takes place at numerous sites scattered throughout the cell, the mitochondria. Typically, these have a volume of 1–10 cubic microns. As the cells are mostly water a 1 cubic micron volume would have the approximate numbers of molecules of fuel gas dissolved in it when in equilibrium with the mixtures at STP as shown in Table I.

TABLE I

| % Fuel Gas Inhaled | # of Molecules in 1 Cubic Micron | Comment |
| --- | --- | --- |
| 0.00005% $H_2$ in air | ¼ | Natural $H_2$ level in air |
| 3% $H_2$ in air | 16,200 | Non-flammable w/buffer |
| 66.7% $H_2$, 33.3% $O_2$ | 360,000 | From electrolysis of water |
| 1.6% $C_2H_2$ in air | 432,000 | Non-flammable w/buffer |
| 5% $C_2H_2$ in air | 1,350,000 | 0.5 L/min $C_2H_2$ in nasal cannula |
| 70% $H_2$, 10% $C_2H_2$, 20% $O_2$ | 3,080000 | Day? Easy enter & exit |
| 80% $C_2H_2$, 20% $O_2$ | 22,000,000 | Night? May be narcotic |
| 1000 mg Vitamin C | approx. 12,000 | Peak level, for comparison |

The present invention will now be described in detail. With regard to the present invention, the term "breathable composition" will refer to a gas mixture available to the lungs for inhalation. Typically, a breathable gas mixture must have an adequate supply of oxygen to support life, and must have a low enough level of toxic species so as not to be toxic.

Breathable compositions can, in general, be supplied in an open circuit, semi-closed circuit or closed circuit manner. In an open circuit system, the breathable composition is supplied for inhalation, and the exhaled gas leaves the system and is not included in the supplied breathable composition. For example, supply of a gas via a nasal cannula would be an open-circuit system; the exhaled gas leaves the vicinity of the body to the general atmosphere.

A closed circuit breathing apparatus involves continuous reuse of the same gas, with only scrubbing or regeneration of the gas to maintain oxygen levels and remove respiration products or toxins.

A semi-closed circuit is intermediate between the open circuit and closed circuit systems, with some recirculation of exhaled gas and release of gas from the system to the general atmosphere.

In the embodiments to be described below, the term "fuel gas compound" is taken to mean any chemical compound which in pure form is a gas and which in pure form can be readily oxidized by oxygen for heat production. Possible fuel gas compounds in the present invention include hydrogen, methane, ethane, propane and acetylene. Other compounds, such as the hydrocarbons ethene, n-butane, isobutane, 1-butene, etc., may also be used.

In a general embodiment of the invention, the invention involves intentionally artificially raising in a tissue of an animal—the term "animal" here being meant to include humans—a concentration of a fuel gas compound to, a level which is above the background level in the tissue. The background level is here taken to mean the level of the fuel gas compound which would be present in the absence of the action taken to raise the level. As discussed above, for example, trace amounts of hydrogen or methane may be naturally found in tissues of animals; these trace levels would represent the background levels. Here, "intentionally artificially" is taken to mean that a particular action of a person is performed for the purpose of raising the concentration of the fuel gas compound.

In another general embodiment, the present invention involves providing an animal ("animal" again taken generically to include humans) with a breathing composition which contains oxygen intentionally supplemented with at least one fuel gas compound. The breathing gas composition may, accordingly, contain more than one fuel gas compound.

Here, the term "intentionally supplemented" means that the breathing composition is artificially prepared to contain greater than a background level in air of the fuel gas compound. For example, it is well known that people are exposed to levels of methane while working in coal mines, dairy farms, oil wells, etc. However, ordinary work in such environments would not be viewed as "intentionally supplemented" for the purposes of this invention, because there is no intention to raise the level of methane above the background level of the air, which in this case may be substantial. Moreover, the presence of methane in these environments would not be considered to be due to artificial supplementation.

Likewise, a person may be exposed to methane or acetylene in air from, for example, a natural gas leak or from use of welding equipment. Although the level of methane or acetylene is artificially greater than the natural background level, such exposure would not be considered "intentional supplementation" because there is no intent to raise the level of the compound in the air breathed.

The present invention may be practiced in a number of more specific embodiments. In one embodiment, the present invention involves providing an animal with a breathing composition which contains oxygen intentionally supplemented with at least one fuel gas compound, with the breathing composition provided at close to atmospheric pressure. This would be in contrast to alternative embodiments in which the breathing gas composition was supplied in a hyperbaric or hypobaric chamber.

In another embodiment of the method of the invention, the breathing composition as described above is continually provided for a period of time greater than one hour. The period of time of continuous providing may be four hours, greater than one day, greater than one week, or even greater than one month.

Typically, the time of continuous providing of the breathing composition will be less than 24 hours in the course of one day. For example, a typical day of use of the method of the present invention might be as follows:

8 hours in bed, supplied with the composition 1 hour for showering, making breakfast, etc., breathing regular air 4 hours in home office or living room, supplied with the composition 0.25 hour auto transit, supplied with the composition 1.5 hour meeting with client, breathing regular air 0.25 hour auto transit, supplied with the composition 3 hours in home office or living room, supplied with the composition 1.5 hours gardening or other outdoor activity, breathing regular air 0.5 hour, making dinner, breathing regular air 4 hours in home office or living room, supplied with the composition In this schedule, the supply of the breathing composition in the car would be using a different apparatus than in the home, as will be described below. In this sample schedule, 19.5 hours of one day are spend breathing the breathing composition of the invention. Thus, in one embodiment, the present invention involves repeatedly breathing the breathable composition of the invention for a time period greater than 15 hours out of each day. Long-term use might be seen by averaging more than 12 hours a day over a 30-day period.

In another embodiment of the method of the invention, the breathing gas composition is provided in an open circuit system. The breathing gas composition may be provided by a nasal cannula or a full-face or oral nasal mask.

In another embodiment, the breathing gas composition may be provided in a chamber enclosing at least a person's head.

In one embodiment of the invention, the breathing gas composition may contain a fuel gas compound or compounds such that the overall composition is explosive. That is, the concentrations of fuel gas compounds and oxygen are such that the composition can undergo rapid, self-sustained combustion if ignited. In this embodiment, the environment around the person will generally be explosion-proofed to avoid igniting the inhaled or exhaled composition. Explosion-proofing generally involves removal of sources of sparks or heat which can cause ignition.

In one embodiment employing a chamber for providing the breathing gas composition, the breathing gas composition is a lighter-than air composition and the chamber is opened at the bottom, with the breathing gas composition being held in the chamber by buoyancy. Compositions containing hydrogen may be used to achieve a light density. Such a composition may have a buoyancy less than 75% that of air, or even less than approximately one-half that of air. One example of a lighter-than-air composition contains approximately 75 to 80% hydrogen and approximately 20% oxygen.

In another embodiment, the breathing gas composition is prepared using a hydrogen/oxygen mixture which is formed by the electrolysis of water.

Specific apparatus embodiments for providing breathing gas compositions will now be described in detail. Turning now to the drawings, FIG. 1 depicts a simple embodiment of an apparatus of the invention for supplying a breathing gas composition containing a fuel gas compound to a person. In FIG. 1, a person is illustrated using a nasal cannula. Constant pressure source 101 is a source of one or more of the fuel gases, and the flow rate of the gas is controlled by flow restrictor 102. An on-off valve 103 is used to turn the flow of gas on or off, and the gas is delivered by nasal cannula 104. The person breathes ambient air along with the supplied fuel gas, therefore creating the breathing gas composition during inhalation, achieving a desired fuel gas compound concentration in the inspired breathing gas.

For example, using acetylene, a restrictor giving a flow of 0.2 L/min, coupled with a normal resting Respiratory Minute Volume (RMV) of 10 L/min, would give an inspired concentration of 2% acetylene in air. A level of 2% is under the explosive limit for acetylene, and it is expected that an explosive level of acetylene should not be achieved when acetylene is supplied in this way.

An alternative to nasal cannula 104 is an oral-nasal mask or a helmet in which the complete breathing gas is supplied at rate sufficient to keep carbon dioxide levels at reasonably low levels. For example, to maintain a carbon dioxide level of 1% of the concentration in the exhaled gas in a helmet having good gas mixing, the effluent rate from the helmet must be 100 times the normal $CO_2$ production rate. Therefore, if $CO_2$ is produced at a typical rate of about 0.5 L/min, a flow-through rate of approximately 50 L/min is required.

Figure 4:
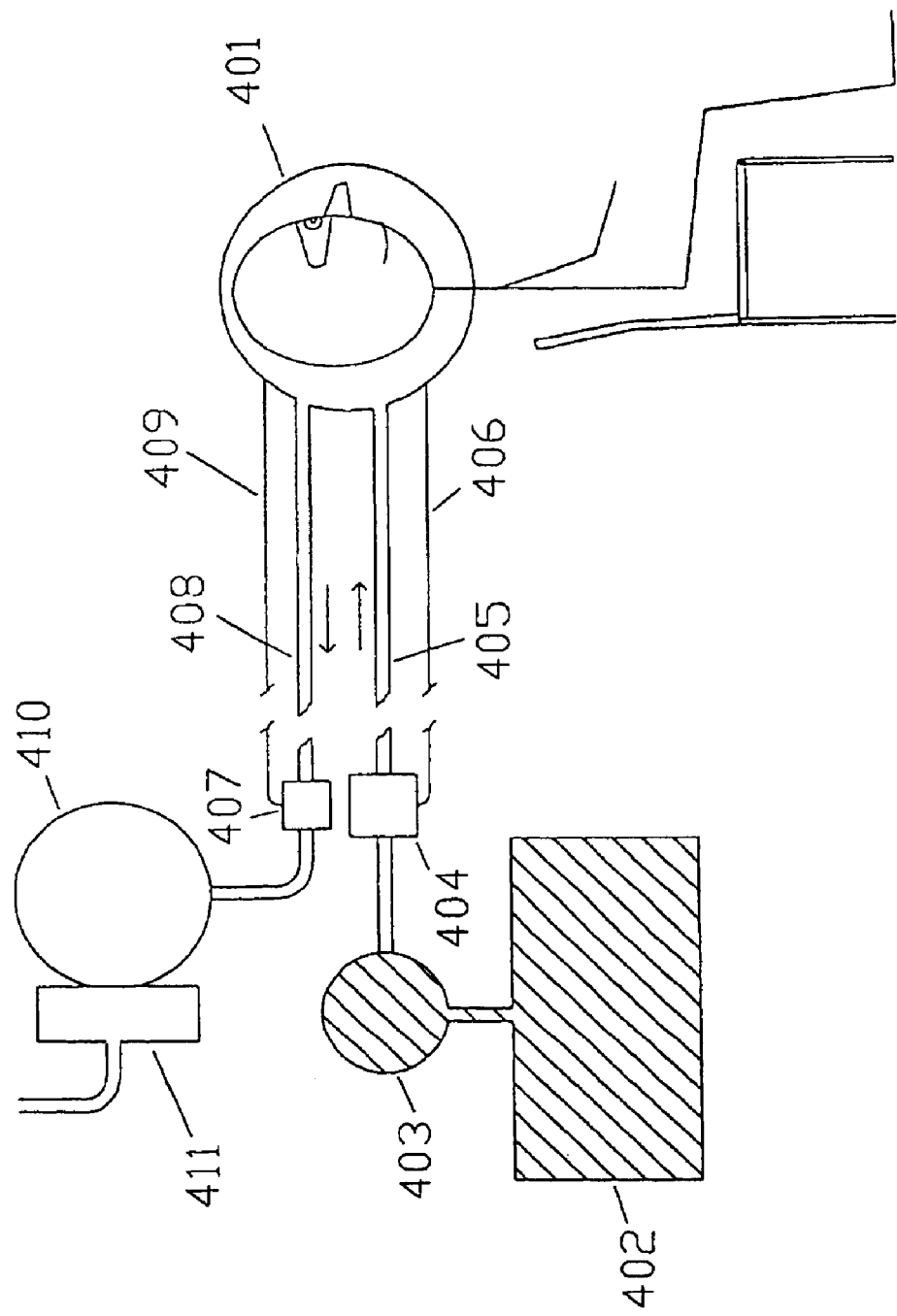
FIG. 4 is a schematic illustration of embodiments of the present invention which are an apparatus and method for delivering a breathing gas composition to an individual using a helmet.

An embodiment employing a closed helmet with an open-circuit supply and exhaust system is shown in FIG. 4. In FIG. 4, a pressurized electrolytic cell 402, in which water is electrolyzed, delivers a hydrogen-oxygen mixture at low pressure to supply buffer tank 403. Thus, pressurized electrolytic cell 402 and supply buffer tank 403, which are represented as shaded, are an embodiment of a supply or source of a respirable gas mixture which includes a fuel gas. In this embodiment, dome-loaded regulator 404 supplies the gas mixture via supply hose 405 to helmet 401. Regulator 404 is controlled by sensing line 406. Dome-loaded back-pressure regulator 407, via return hose 408, controls the pressure in the helmet to be a negative pressure of approximately ¼ to 1" of water, and back-pressure regulator 407 is controlled by sensing line 409. Return buffer tank 410 smoothes the flow and provides a more even inlet pressure to explosion-proof suction compressor 411.

The supply pressure of electrolytic cell 402 is low, typically a few PSI (pounds per square inch). The supply hoses and regulators are large and the flows are relatively slow. Likewise, the pressure change caused by suction compressor 411 is set on the order of 3 PSI, providing a compression ratio of less than 1.4. This leads to a low heat of compression and avoids compression being a source of ignition. The return system also uses large, slow-flow return components.

In operation, the system requires a slight negative pressure for the helmet to supply breathing gas. Thus, the system starts automatically when the helmet is donned and stops when it is doffed.

Electrolytic cell 402 delivers 33.3% oxygen by volume from the electrolysis of water. By constructing a semi-closed system, only enough production by the electrolytic cell is required to maintain adequate oxygen supply. Thus the delivery from electrolytic cell 402 can be reduced by about 85% relative to the open circuit, system described above. Moreover, a higher partial pressure of hydrogen can be delivered for respiration, with levels of 75 to 80% being possible. In addition there would be lower power consumption and less effluent.

Figure 2:
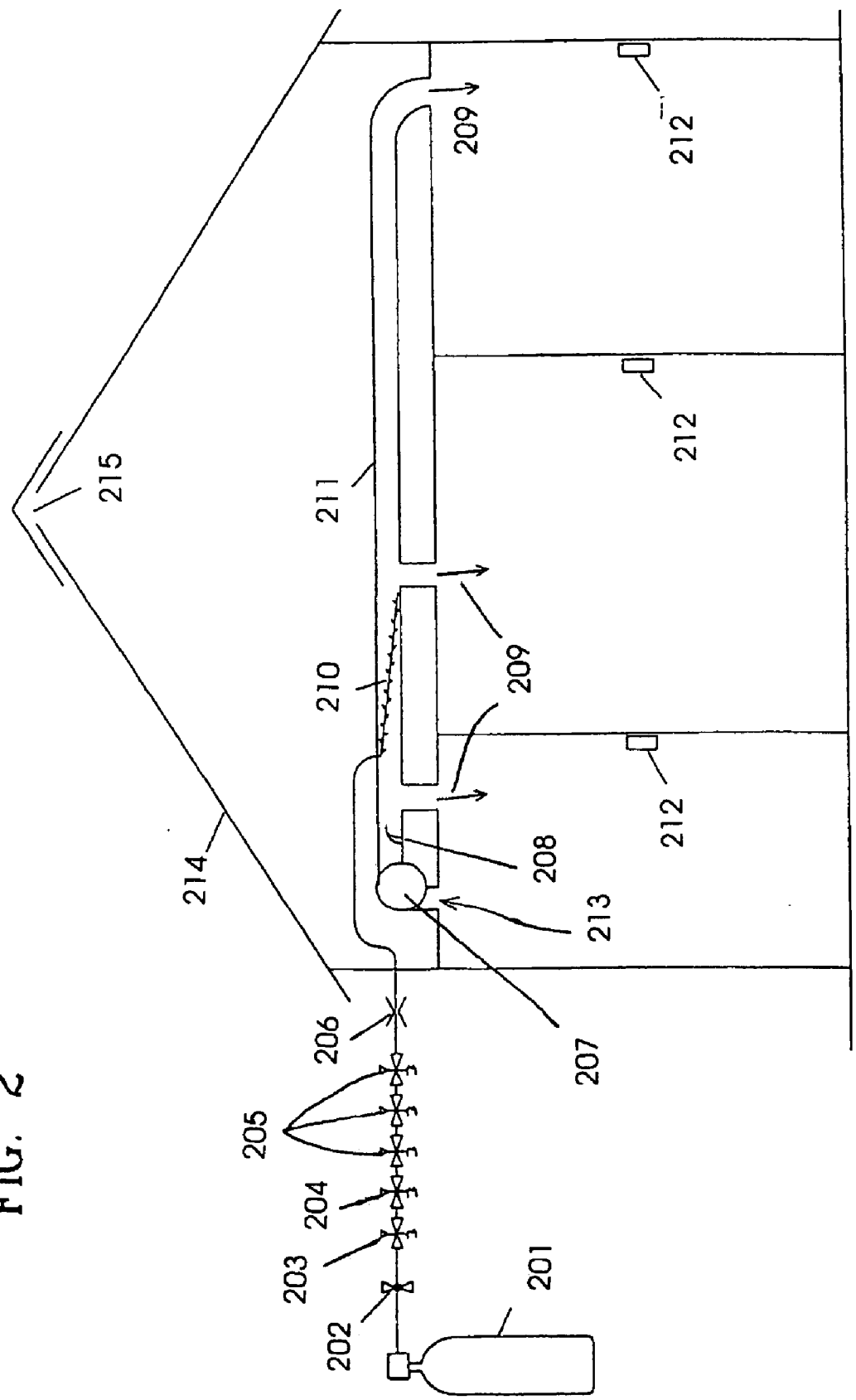
FIG. 2 is a schematic illustration of embodiments of the present invention which are an apparatus and method for delivering a breathing gas composition to a building.

FIG. 2 shows an alternative supply apparatus of the invention which is designed to supply the fuel gas to create a breathing gas composition for a house or other building. House 214 has the following elements in the air-conditioning/heating system: explosion-proofblower 207, ducting 211, return inlet to the blower 213, and outlets 209 into the various rooms. Constant-pressure source 201 of one or more of the fuel gases supplies the desired fuel gas or fuel gas mixture, and manual on-off valve 202 allows a complete shut-off of the gas source. Turning on blower 207 opens normally-closed valve 203. When the flow of air in duct 211 is detected by flow-sensor 208, valve 204 is opened. Valve 204 remains closed when there is no flow in the duct. Several fuel-gas sensors 212 are illustrated; in this embodiment one is installed in each room. Each fuel-gas sensor 212 is linked to and controls one of valves 205. Valves 205 are designed to remain closed until signaled to open. Vent 215 is located in the attic to allow the escape of fuel gases lighter than air.

Here, blower 207 is explosion-proof, that is, designed to produce no sparks which might cause ignition, as a safety feature. However, in normal use the blower should not contact air which contains fuel gas at above the explosive limit.

When all of valves 203, 204, and 205 are open, fuel gas flow proceeds to flow restrictor 206, and on to flow-diffuser 210, downstream of blower 207 in ducting 211. Restrictor 206 is selected so that on a wind-free day a desired percentage of fuel gas compound in the air in house 214 is maintained when the fuel gas is flowing 75% of the time. This arrangement is a safety feature to avoid development of an explosive level of an explosive level of fuel gas. For example, for acetylene, using a desired maintenance level of 1.6% in air, a failure of all other systems resulting in flow of gas 100% of the time will still not result in an explosive condition.

In normal use, fuel-gas sensors 212 also prevent the formation of an explosive level of gas by shutting down corresponding valve 205 if the gas level rises above a preset level. The apparatus of FIG. 1 therefore allows the continuous maintenance of a concentration of fuel gas in a house at a desired level below the explosive limit. Occupants of the house can thus be exposed to the fuel gas for substantial periods of time.

Figure 3:
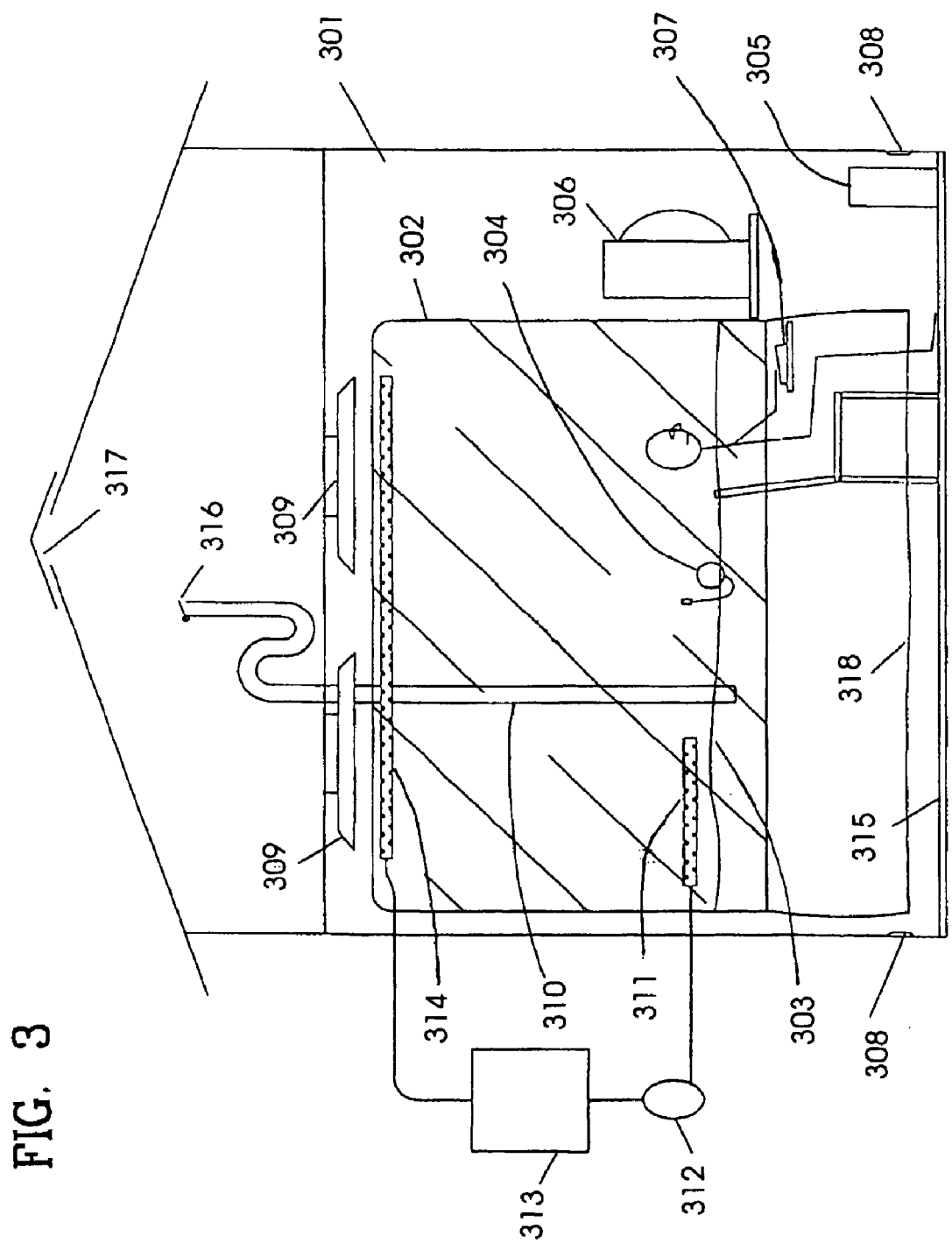
FIG. 3 is a schematic illustration of embodiments of the present invention which are an apparatus and method for delivering a breathing gas composition to a confined region.

FIG. 3 depicts an alternative embodiment of the invention, which is an apparatus for delivering the fuel gas to a controlled space which is smaller than the entire building. In FIG. 3, inside office 301 is transparent container 302, which is open at the bottom for ingress and egress of a person. Here, the transparent container is at least large enough to hold one person, and may occupy a substantial portion of a room.

This embodiment employs the principle that mixtures of hydrogen, methane or acetylene with oxygen are lighter than air, since the molecular weights of these fuel gases are less than the average molecular weight of air, which is about 29 g/mol. This is particularly true at higher concentrations of the fuel gas. The breathing gas used in this embodiment may be a potentially explosive mixture of hydrogen, acetylene, and oxygen, with a density approximately than half that of air. This composition of breathing gas can be taken to consist essentially of hydrogen, acetylene and oxygen. Here, "consisting essentially of" is taken to mean that hydrogen, acetylene and oxygen are the primary and active components, but small amounts of impurities not detracting from the essential quality of the composition may be present. Thus, small amounts of nitrogen, which is essentially inert, as well as carbon dioxide and other impurities which may accumulate in breathed gas, may be present, as long as the gas retains its low density and reactive oxygen species-removing property. Generally, oxygen levels will be kept at about 20% as in air. Being substantially lighter than air, this gas mixture is held in place by in relative buoyancy and does not tend to drift down and out of container 302.

In FIG. 3, reference numeral 303 indicates the division between the gas mixture and the air below it, and a tethered and relatively impermeable balloon 304, filled with the mixture, floating on the air layer, acts as a level indicator.

Flexible skirt 318, prevents 'sloshing' of the mixture under the lip of container 302 and into the room. An overflow pipe 310 with its entry several inches above the bottom lip of container 302 and several inches below the level of the person's nose and mouth, leads to non-return flap valve 316 located above any possible ignition sources, where low density will cause any escaping mixture to vent harmlessly through attic vent 317 and into the atmosphere.

The various contents of office.301 near the container are all grounded or explosion-proof as appropriate and any other heat sources which could trigger an explosion are eliminated. The contents may include, for example, computer 305, monitor 306, explosion-proofed keyboard 307, electrical outlets 308, and the lighting system 309.

To enter container 302, the person first kneels or lie on antistatic mat 315, which covers the entire floor of office 301. Thus any existing static charge is dissipated before entering the bubble of explosive gas.

The gas mixture inside container 302 is circulated and treated. Explosion-proof blower 312 takes the gas mixture from inlet muffler 311, located approximately at mouth level, feeds the gas mixture through life support system 313, and then circulates the mixture back into container 302 via muffler/diffuser pipe 314. Life support system 313 scrubs $CO_2$, controls temperature and humidity, adds oxygen, and contains a secondary loop system for scrubbing nitrogen, argon, oils, and other secondary contaminants. The life support system 313 also provides all appropriate alarms, readouts, and redundancies for a system providing life support. For example, an alarm may indicate any level of a toxin in the gas mixture, or any failure of the system.

Container 302 is of a size such that changes in vital life support parameters, in particular due to respiration of the person, will generally be extremely slow. Thus, failure of any or all elements of life support system 313 will not endanger the occupant of the container over the course of a single day.

The system as shown in FIG. 3 is illustrated as a semi-closed system. A fully closed system, such as a space-suit, bag or tent may also be used. Alternatively, it is possible to deliver a potentially flammable gas mixture in an open-circuit system, in which the gas mixture would be constantly supplied and vented away.

When using the embodiment of the invention shown in FIG. 3, it is essential that explosion be prevented. Thus, this embodiment may only be used in a carefully controlled environment in which all potential sources of ignition are eliminated.

The present invention therefore provides a method and apparatus for reducing reactive oxygen species in humans by providing a breathing gas containing a level of a fuel gas. Although the present invention has been described in detail, it should be understood that various changes, substitutions and alterations may be made without departing from the spirit and scope of the invention as defined by the appended claims.

What is claimed is:

1. A method of providing protection from reactive oxygen species, the method comprising the steps of:
   preparing a breathable composition comprising oxygen intentionally supplemented with a fuel gas comprising at least one hydrocarbon fuel gas;
   providing said breathable composition to an animal on land while the animal is surrounded by a gaseous environment; and
   within said animal, scavenging said reactive oxygen species with said fuel gas.

2. The method of claim 1, said animal being a human.

3. The method of claim 1, further comprising providing the animal with the breathable composition continually for a period of time greater than one hour.

4. The method of claim 3, further comprising providing the animal with the breathable composition continually for a period of time greater than one day.

5. The method of claim 4, further comprising providing the animal with the breathable composition continually for a period of time greater than one month.

6. The method of claim 3, further comprising providing the animal with the breathable composition continually for a period of time greater than 4 hours.

7. The method of claim 3, further comprising providing the animal with the breathable composition for a cumulative time of greater than 15 hours in one day.

8. The method of claim 3, further comprising providing the animal with the breathable composition for an average of greater than 12 hours a day over 30 consecutive days.

9. The method of claim 1, said fuel gas being selected from the group consisting of, methane, ethane, propane, acetylene, ethene, n-butane, isobutane, 1-butene, and a combination thereof.

10. The method of claim 1, said breathable composition being an explosive composition.

11. The method of claim 10, further comprising explosion-proofing the environment where the breathable composition is being provided to prevent ignition of the breathable composition or exhaled gas.

12. The method of claim 1, the breathable composition being provided at or near atmospheric pressure.

13. The method of claim 12, the providing of the breathable composition being performed using an open circuit apparatus.

14. The method of claim 1, the providing of the breathable composition being performed using a closed circuit apparatus.

15. The method of claim 1, the providing of the breathable composition being performed using a semi-closed circuit apparatus.

16. The method of claim 1, the step of providing further comprising the steps of:
   positioning the animal in a building with a ventilation system; and
   supplying said fuel gas into the ventilation system to provide the breathable composition inside the building.

17. The method of claim 1, wherein the step of providing said-breathable composition simultaneously with the step of preparing said breathable composition by supplying said fuel gas is supplied to a respiratory tract of the animal and said oxygen is supplied from ambient air so that, upon inhalation of the fuel gas and the ambient air, said breathable composition is prepared and provided to the animal.

18. The method of claim 17, further comprised of maintaining a selected concentration of the fuel gas in the breathable composition by regulating a rate of supply of said fuel gas to the respiratory tract.

19. The method of claim 1, further comprised of supplying the breathable composition to the animal via an oral-nasal mask or a helmet.

20. The method of claim 1, further comprising the step of providing the breathable composition under a hyperbaric condition.

21. The method of claim 1, with said fuel gas being acetylene.

22. The method of claim 1, preparing said breathable composition by delivering ambient air together with said fuel gas.

23. The method of claim 1, further comprising the step of providing the breathable composition under a hypobaric condition.

24. The method of claim 1, further comprising the steps of:

filling a first chamber having an open bottom with the breathable composition, said first chamber being positioned in a second chamber, said breathable composition being lighter than an ambient air so that said breathable composition is held in said first chamber; and positioning the animal in the first chamber with the open bottom so that the animal breathes the breathable composition.

25. The method of claim 24, further comprising:

explosion-proofing the environment in the first and second chambers.

26. The method of claim 25, further comprised of said breathable composition being an explosive composition.

27. The method of claim 26, with said breathable composition consisting essentially of hydrogen, acetylene and oxygen.

28. The method of claim 26, with said breathable composition consisting essentially of hydrogen and oxygen.

29. The method of claim 26, with said breathable composition having a density less than 75% that of air.

30. The method of claim 26, with said first chamber further comprising a flexible skirt suspended from a lip defined by the open bottom of the first chamber.

31. The method of claim 26, wherein said first chamber is further comprised of an overflow pipe extending from an entry opening above the open bottom of the first chamber through the top of the first chamber, and said second chamber is further comprised of a check valve at the top of the overflow pipe, said check valve is located in a region providing ventilation.

32. The method of claim 31, further comprising:

positioning an inlet muffler inside the first chamber below the approximate height of a mouth of the animal in the first chamber;

purifying the breathable composition drawn by the inlet muffler by locating a life support system outside the first chamber and connecting the life support system to said inlet muffler; and purifying breathable composition to supplied to the first chamber by installing a muffler diffuser pipe inside the first chamber and connecting the pipe to the life support system.

33. The method of claim 32, said life support system further comprising:

a $CO_2$ scrubber;

a temperature and humidity control;

an oxygen supply supplementing oxygen;

a secondary loop scrubbing nitrogen, argon, oils and other contaminants; and an alarm system alerting when there is a failure in the system.

34. The method of claim 26, further comprising:

an antistatic mat on a floor under the first chamber.

35. The method of claim 24, further comprising:

scrubbing an exhaled gas of the first chamber to remove carbon dioxide.

36. The method of claim 24, said breathable composition comprising at least 66% hydrogen by volume.

37. The method of claim 24, said breathable composition comprising hydrogen and acetylene.

38. The method of claim 24, the breathable composition in the first chamber having a density less than about 75% of the ambient air.

39. A method of providing protection from reactive oxygen species, the method comprising the steps of:

preparing a breathable composition comprising oxygen intentionally supplemented with acetylene;

providing an animal on land while surrounded by a gaseous environment with said breathable composition; and within said animal, scavenging said reactive oxygen species with said acetylene.

40. The method of claim 39 with said oxygen being supplied from an ambient air.

41. The method of claim 39, with said breathable composition further intentionally supplemented with a fuel gas.

42. The method of claim 41, said fuel gas being selected from the group consisting of hydrogen, methane, ethane, and propane.

43. A method of providing protection from reactive oxygen species, the method comprising the steps of:

preparing a breathable composition consisting essentially of ambient air intentionally supplemented with hydrocarbon fuel gas;

providing said breathable composition to an animal on land; and within said animal, scavenging said reactive oxygen species with said hydrocarbon fuel gas.

* * * * *